United States Patent [19]

Rozzell

[11] Patent Number: 4,518,692

[45] Date of Patent: May 21, 1985

[54] PRODUCTION OF L-AMINO ACIDS BY TRANSAMINATION

[75] Inventor: J. David Rozzell, Cambridge, Mass.

[73] Assignee: Genetics Institute, Inc., Boston, Mass.

[21] Appl. No.: 528,730

[22] Filed: Sep. 1, 1983

[51] Int. Cl.³ .................. C12P 13/06; C12P 13/04; C12P 13/22; C12P 13/08; C12P 13/12

[52] U.S. Cl. .................. 435/116; 435/106; 435/108; 435/113; 435/115

[58] Field of Search .................. 435/106–116

[56] References Cited

U.S. PATENT DOCUMENTS

| | | | |
|---|---|---|---|
| 3,036,958 | 5/1962 | Asai et al. | 195/29 |
| 3,183,170 | 5/1965 | Kitai et al. | 435/116 X |
| 3,458,400 | 7/1969 | Chibata et al. | 435/116 |
| 3,463,704 | 8/1969 | Okumura et al. | 435/116 |
| 3,767,528 | 10/1973 | Nagasaki et al. | 195/30 |
| 3,898,128 | 8/1975 | Chibata et al. | 435/116 X |
| 4,304,858 | 12/1981 | Wandrey et al. | 435/115 |

OTHER PUBLICATIONS

Tosa et al., in Applied Microbiology, vol. 27, pp. 886–889 (1974).

Umbarger et al., in Annual Review of Microbiology, vol. 47, pp. 533–606 (1978).

Herbert, "Oxalacetic Carboxylase of *Micrococcus lysodeikticus*", Methods in Enzymology, vol. 1, pp. 753–757.

*Primary Examiner*—Lionel M. Shapiro
*Attorney, Agent, or Firm*—Sewall P. Bronstein; George W. Neuner

[57] ABSTRACT

A process is described for producing alpha amino acids or derivatives thereof. The process comprises reacting an alpha-keto acid with L-aspartic acid in the presence of transaminase enzyme to produce (1) an alpha amino acid corresponding to said alpha-keto acid and (2) oxaloacetate; and decarboxylating said oxaloacetate.

17 Claims, No Drawings

PRODUCTION OF L-AMINO ACIDS BY TRANSAMINATION

This invention relates to the production of alpha amino acids and derivatives thereof, and in particular, to the production of L-amino acids and their derivatives by transamination between L-aspartic acid and alpha-keto acid compounds corresponding to the desired amino acids.

BACKGROUND OF THE INVENTION

Amino acids currently have application as additives to animal feed, nutritional supplements for human food, components in infusion solutions, and synthetic intermediates for the manufacture of pharmaceuticals and agricultural chemicals. L-glutamic acid is used as a flavor enhancer for food with a world market of over 1 billion dollars annually. L-lysine and methionine are large volume additives to animal feed, and L-tryptophan and L-threonine have similar potential applications. L-phenylalanine and L-aspartic acid have very important markets as key components in the manufacture of the sweetener aspartame. Infusion solutions require a range of amino acids including those essential in human diets.

Methods currently in use for the production of amino acids include extraction, chemical synthesis followed by resolution, fermentation and enzymatic synthesis (biocatalysis). Extraction procedures require extensive purification of the amino acid of interest from protein hydrolyzates. With chemical synthetic methods, normally a racemic mixture is formed, and the resolution to produce the optically active product is often costly and inefficient. Fermentation, while overcoming many of the disadvantages inherent in the previously mentioned methods, suffers from problems of slow rates of conversion, dilute solutions, costly purifications, and very high capital costs. Biocatalysis offers the potential for lower cost production in many cases primarily because of the significantly reduced capital requirements, lower purification costs due to the absence byproducts in the product stream, and higher rates of conversion of substrates to products because fewer enzymatic steps are involved.

Some biocatalytic processes are currently in use. For example, L-aspartic acid is produced in commercial quantities by the reaction of fumaric acid with ammonia in the presence of the enzyme aspartase. See Tosa et al, Appl. Microbiol. 27, 886–9 (1974). L-phenylalanine can be produced by enzymatic synthesis from cinnamic acid and ammonia using the enzyme phenylalanine-ammonia lyase. L-alanine can be synthesized from L-aspartic acid by enzymatic decarboxylation. See. U.S. Pat. Nos. 3,458,400 and 3,463,704. These processes are useful for the production of the individual amino acids listed. However, none of these processes is based on a general enzymatic technology broadly applicable to the production of many amino acids.

One enzymatic process broadly applicable to the production of many amino acids is described in U.S. Pat. No. 3,183,170. In the process of U.S. Pat. No. 3,183,170 L-glutamic acid and a keto acid are combined with transaminase to produce alpha-keto glutaric acid and L-amino acid. The alpha-keto glutaric acid is continuously reduced to L-glutamic acid in the presence of a multi enzyme system, hydrogen gas, and a nitrogen souce, such as inorganic ammonium salt, organic ammonium salt, ammonium hydroxide, ammonia gas, or urea. The L-glutamic acid thus produced is recycled thus enabling the production of large amounts of L-amino acid with a small quantity of L-glutamic acid. However, this multienzyme system is difficult to operate on a commercial scale because it requires the cofactor NAD/NADH which is expensive, hydrolytically unstable and sensitive to oxygen and to light. Thus, a general enzymatic technique broadly applicable to the production of many amino acids is still desired.

SUMMARY OF THE INVENTION

The present invention provides an enzymatic process capable of producing many alpha amino acids from the readily available L-aspartic acid (or L-aspartate). In the process of the present invention, L-aspartic acid and an alpha-keto acid are reacted in the presence of a transaminase to form L-amino acid and oxaloacetate, followed by decarboxylation of said oxaloacetate to form pyruvic acid. The decarboxylation of oxaloacetate drives the reaction to completion. Yields of 95% or more of the desired L-amino acid are readily obtained. The by-product, pyruvic acid, is readily separated from the L-amino acid and is highly marketable.

DETAILED DESCRIPTION OF THE INVENTION

In accord with this invention a class of enzymes known as transaminases (aminotransferases) catalyze the general reaction:

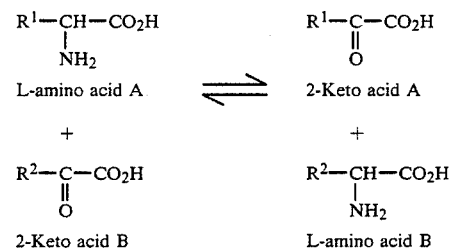

By choosing the proper 2-keto acid precursor B, a desired L-amino acid B can be produced by transamination using another L-amino acid A as the amino donor. As a byproduct of the reaction, a second 2-keto acid A is produced along with the desired L-amino acid B. The advantages of this transamination technology are:

1. L-amino acids are produced specifically.
2. The 2-keto acid precursors are conveniently available from chemial synthesis.
3. The rates of reaction are relatively rapid.
4. The capital costs are lower than for a fermentation process.
5. The technology is general because transaminases with varying selectivities are available, e.g. aromatic amino acid transaminases, branched chain amino acid transaminases, transaminases specific for amino acids having acidic side chains, etc. Such transaminases can be prepared, for example, from the following microorganisms: *Escherichia coli* (*E. coli*), *Bacillus subtilis, Achromobacter eurydice, Klebsiella aerogenes,* and the like. Transaminases useful in the practice of this invention are also described by H. E. Umbarger in Annual Rev. Biochem., Vol. 47, pp. 533–606 (1978).

The single greatest disadvantage of this general method is that the equilibrium constant for the transamination reaction as written above is about 1.0. As a result, the yield of the desired amino acid for the reaction as written will never exceed approximately 50%. The key to the development of a commercially successful transamination process for the production of amino acids is overcoming the problem of incomplete conversion of 2-keto acid B to the desired L-amino acid B.

This problem is solved by the present invention by using L-aspartic acid as the amino donor (L-amino acid A) and by converting the byproduct (2-keto acid A), i.e. oxaloacetate, by an irreversible reaction, decarboxylation, to pyruvic acid.

Preferably, the irreversible decarboxylation of oxaloacetate is coupled to the transamination reaction. Thus, the transamination reaction is driven to completion, as shown below:

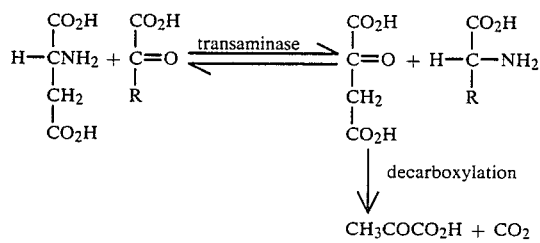

By coupling the decarboxylation of the oxaloacetate to the transamination reaction in accord with this invention, the production of L-amino acids in high yield can be obtained by this biocatalytic method. Using this method, the conversation of the 2-keotacid precursor B to the desired L-amino acid B in yields approaching 100% have been achieved.

The decarboxylation of oxaloacetate can be catalyzed either thermally; chemically by various metal ions, amines and/or acids; or preferably enzymatically by the enzyme oxaloacetate decarboxylase (OAD) E.C. 4.1.1.3. Oxaloacetate decarboxylase from any source can be used. Examples of sources of oxaloacetate decarboxylase useful in the practice of the present invention are, for instance, Micrococcus luteus, renamed from Micrococcus lysodeikticus (see Methods in Enzymology 1, 753-7 (1955) which is incorporated by reference, Pseudomonas putida (see Biochem. Biophys. Acta 89, 381-3 (1964) which is hereby incorporated by reference), and Azotobacter vinelandii (see J. Biol. Chem. 180, 13 (1949) which is hereby incorporated by reference), etc. Also, any other enzyme having a ozaloacetate decarboxylase activity but not usually regarded as an "oxaloacetate decarboxylase" may be used such as, for instance, pyruvate kinase, malic enzyme, etc. The activity of oxaloacetate decarboxylase can be enhanced by adding metal ions such as, for example, $Mn^{++}$, $Cd^{++}$, $Co^{++}$, $Mg^{++}$, $Ni^{++}$, $Zn^{++}$, $Fe^{++}$, $Ca^{++}$ and the like.

The process of this invention can thus be used for the production of a large variety of L-amino acids by choosing the proper 2-keto acid precursor and an enzyme capable of transaminating it with L-aspartic acid. For example, the amino acid L-phenylalanine, a key component in the manufacture of the sweetener aspartame, has been prepared by this method in high yield from phenylpyruvate and L-aspartic acid using a transaminase isolated from E. coli and an oxaloacetate decarboxylase isolated from either Pseudomanas putida or Micrococcus luteus. Similarly, using these same enzymes, p-hydroxyphenylpyruvate was converted into L-tyrosine, indole-3-pyruvate or 3-(3-indolyl)pyruvic acid has been converted into L-tryptophan, and 2-oxo-4-methylpentanoic acid has been converted into L-leucine. By using transaminases with different specificities, 2-oxo-3-methylpentanoic acid was transaminated to L-isoleucine, 2-oxo-3-methylbutanoic acid to L-valine, pyruvic acid to L-alanine, 3-hydroxypyruvate to L-serine, glyoxylic acid to glycine, and 2-oxo-4-thiomethylbutanoic acid to L-methionine.

Thus, R in the keto acid starting material $RCOCO_2H$ can be selected from a wide variety of substituents including, for example, hydrogen, substituted and unsubstituted lower alkyl, substituted and unsubstituted lower aryl, and heterocyclic groups.

The term "lower alkyl" as used herein means both straight and branch chain alkyl groups having from one to about six carbon atoms. Substituted lower alkyl groups means lower alkyl groups substituted with hydroxy, mercapto, carbamoyl, carboxy, amino, amidino and R'-thio (where R' is lower alkyl) groups such as found in natural amino acids.

The term "lower aryl" as used herein means phenyl and benzyl groups. Substituted lower aryl groups includes phenyl and benzyl groups substituted with groups such as those listed above for lower aklyl.

Heterocyclic groups as used herein means

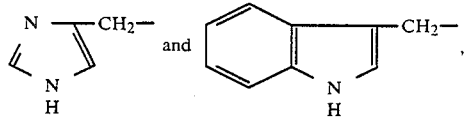

and the like.

Examples of such R groups suitable for the practice of the present invention include: hydrogen, methyl, isopropyl, isobutyl, sec-butyl, benzyl, phenyl-1-(methylthio)ethyl, hydroxymethyl, mercaptomethyl, p-hydroxybenzyl, p-hydroxyphenyl, carbamoylmethyl, carbamoylethyl, aminobutyl, amidinoaminopropyl, indolyl, 3-indoylmethyl, imidazoyl, 4-imidazoylmethyl, and the like.

The byproduct of the decarboxylation of oxaloacetate, pyruvic acid, is a valuable commercial product and can be recovered from the product stream by any method described in the prior art, such as acidification and distillation, ion exchange, solvent extraction, and the like.

The enzymes can be added to the reaction mixture in whole cells, crude cell lysates, as partially purified enzyme or purified enzyme. Preferably purified enzymes are used, either immobilized or in solution, because the conversion rates per unit of enzyme are higher. The enzymes can be purified by techniques well known to those skilled in the art. Examples of purification of oxaloacetate decarboxylase from Micrococcus luteus and Pseudomonas putida are described by Herbert, Methods in Enzymology 1, pp. 753–57 (1955) and by Morton et al., Biochem. Biophys. Acta. 89, pp. 381–83 (1964).

The enzymes can be used in solution or as immobilized enzymes, as aforesaid, in the practice of this invention. One example of an immobilized enzyme system is described by Weetall et al., Methods in Enzymology 34, pp. 59–72 (1974), which is hereby incorporated by reference. Weetall et al. describe a method for immobilizing enzymes on glutaraldehyde activated controlled pore glass beads (Corning).

In accord with this method, transaminase was coupled to the glass particles by reacting the enzyme with the activated glass particles at 0°–5° C. for 2 hours in a phosphate buffer solution having a pH of 7.0. The coupled enzyme can be used directly or first reacted with 1% sodium borohydride to stabilize the covalent link between the enzyme and the activated glass.

Other suitable substrates for immobilizing enzymes for the practice of this invention include porous ceramic, sepharose, diethylaminoethyl cellulose, and the like. These substances can be activated, if desired, by techniques well known in the art.

The oxaloacetate decarboxylase is either immobilized separately, or first mixed with the transaminase and the mixture co-immobilized. Glass beads on which the enzymes had been covalently attached by the aforedescribed procedures were suspended in a solution containing 10 mM phenylpyruvate, 10 mM L-aspartic acid, 1 mM $MgCl_2$ or $MnSO_4$, pH adjusted to the range 4.0–10.0 and most preferably between 5.5 and 8.5. When all the phenylpyruvate had been consumed, the solution was filtered away from the glass beads and the products L-phenylalanine and pyruvic acid isolated and purified by conventional methods.

The reaction of L-aspartic acid to produce L-amino acids and pyruvic acid can be monitored if desired. A general assay which is applicable to the assay of all transamination reactions using L-aspartic acid as the amino donor regardless of the 2-keto acid precursor that is used is the following: L-aspartic acid, a 2-keto acid, transaminase, NADH, and the enzyme malic dehydrogenase (available commercially) are dissolved in solution of phosphate buffer as a pH between 6.0 and 9.0; the change in the absorbance at 340 nm ($A_{340}$) with time is measured. This change in the absorbance at 340 nm corresponds to the consumption of NADH during the reduction of oxaloacetate, formed from L-asparate during the transamination reaction.

As an alternative, for instance, the conversion of phenylpyruvate to L-phenylalanine can be conveniently assayed by taking aliquots from the reaction mixture containing, for instance, transaminase, phenylpyruvate, L-aspartate, oxaloacetate decarboxylase, and metal ions, diluting them into a solution of 2.5% sodium hydroxide in water (w/v), and measuring the absorbance at 320 nm. Dilution into sodium hydroxide causes rapid achievement of the equilibrium between the keto and enol forms of phenylpyruvate. The extinction coefficient at 320 nm for the equilibrium mixture is 17500 $M^{-1} cm^{-1}$. Thus, the conversion of phenylpyruvate into L-phenylalanine can be quantitated rapidly. This assay can be corroborated by measuring L-phenylalanine qualitatively by paper chromatography and quantitatively using an amino acid analyzer.

Similar techniques can be used to assay for the conversion of other 2-keto acids into the corresponding L-amino acids. The transamination of p-hydroxyphenylpyruvate to L-tyrosine can be monitored by diluting aliquots removed from the reaction mixture into 2.5% NaOH and measuring the absorbance at 331 nm (extinction coefficient of 19900 $M^{-1} cm^{-1}$, and the conversion of indole-3-pyruvate into L-tryptophan can likewise be followed by measuring the absorbance at 328 nm (extinction coefficient of 10000 $M^{-1} cm^{-1}$).

The invention will now be further illustrated by the following examples which are given here for illustrative purposes only and are not intended to limit the scope of the invention.

EXAMPLE 1

Preparation of Aromatic Acid Transaminase

*E. coli* K-12 maintained on L-broth plates was innoculated into 2.0 liter shake flasks containing 500 ml of the medium listed below:

| | |
|---|---|
| $KH_2PO_4$ | 5 g/Liter |
| $K_2HPO_4$ | 5.56 g/liter |
| $(NH_4)_2SO_4$ | 2 g/liter |
| $MgSO_4$ | 75 mg/liter |
| $Na_3$ (citrate).$2H_2O$ | 1 g/liter |
| *Trace Metals | 3 ml/liter |
| Glucose | 10 g/liter |

*Preparation of Trace Metals Solution

| Metal Salts | Amount | Final concentrations |
|---|---|---|
| $FeCl_3.6H_2O$ | 27 g/l | 300 uM |
| $ZnCl_2$ | 1.3 g/l | 30 uM |
| $CoCl_2.6H_2O$ | 2 g/l | 25 uM |
| $Na_2MoO_4.2H_2O$ | 2 g/l | 25 uM |
| $CaCl_2.2H_2O$ | 1 g/l | 20 uM |
| $CuCl_2.2H_2O$ | 1.27 g/l | 22 uM |
| $H_3BO_3$ | 0.5 g/l | 24 uM |
| HCl (conc) | 100/ml/l | 3.6 uM |

Growth was at 37 C. for 15 hours. These flasks were used to innoculate 14 liter Biolafitte fermenters (1 liter of shake flask culture into 7 liters) containing 7 liters of the growth medium listed below:

| | |
|---|---|
| $KH_2PO_4$ | 2.0 g/liter |
| $K_2HPO_4$ | 3.6 g/liter |
| $(NH_4)_2SO_4$ | 750 mg/liter |
| $Na_3$(citrate).$2H_2O$ | 1 g/liter |
| Trace metals | 3 ml/liter |
| Pump in glucose as needed. | |

Growth was at 37° C. with aeration at 300 rpm and the pH was maintained at 6.9 by titration with ammonium hydroxide. The cells was harvested by centrifugation at 4000 rpm and frozen at −10° C. until needed.

Purification of the Aromotic Acid Transaminase

All steps were carried out at 4° C. Centrifugations were carried out in a Sorvall RC2B centrifuge.

1. *E. coli* K-12 cells (80 g wet weight) were resuspended in 200 ml of an aqueous buffer solution, pH 7.0, containing 200 mM potassium phosphate, 1 mM ethylenediaminetetraaccetic acid (EDTA) disodium salt, 1 mM beta-mercaptoethanol, 1 mM pyridoxal phosphate, and 0.02% (weight/volume) sodium azide. The cells were sonicated using a Heat Systems—Ultrasonics Cell Disruptor with 4 one minute bursts, power setting 9. The cell debris was separated by centrifugation at 12,000 rpm for 20 minutes.

2. The crude extract (supernatant from step 1) was made 1.25% weight/volume in streptomycin sulfate by adding the appropriate amount of a 40% streptomycin sulfate solution prepared in the buffer of step 1. The mixture was stirred slowly for 20 minutes then centrifuged at 12,000 rpm for 20 minutes. The precipitate was discarded.

3. The protein in the supernatant from step 2 was fractioned by the addition of ammonium sulfate. Crystalline ammonium sulfate was added with stirring until a concentration 40% of saturation was attained and the protein precipitate was centrifuged and discarded. Additional ammonium sulfate was added with stirring until a concentration 70% of saturation was attained and the protein precipitate was centrifuged, collected, and redissolved in the minimum amount of a buffer, pH 6.5, containing 0.03M sodium phosphate, 1 mM ethylenediaminetretraacetic acid disodium salt, 1 mM beta-mercaptoethanol, and 0.02% (weight/volume) sodium azide. This solution was dialyzed against 2 liters of the same buffer (18 hours, 2 changes of buffer).

4. A DEAE-cellulose column (Whatman DE-52, 1.6×30 cm) was equilibrated with the buffer from step 3. The sample was loaded on the column and washed until no more protein could be detected in the effluent as measured by the $OD_{280}$ (<0.02). A 0–0.5M NaCl linear gradient was established, 250 ml total volume, flow rate=4 ml/10 minutes/fraction. Transaminase activity eluted between 0.09 and 0.2M NaCl and was pooled and dialyzed against 2×2 liters of a buffer, pH 6.5, containing 0.03M sodium phosphate, 1 mM ethylenediaminetetraacetic acid disodium salt, 1 mM beta-mercaptoethanol, 0.02 mM pyridoxal phosphate.

5. The transaminase solution was loaded onto a column of hydroxyapatite (2.6×30 cm) and equilibrated in the dialysis buffer of step 4. The transaminase activity was not retained by the column and was concentrated to approximately 4 ml using an Amicon ultrafiltration apparatus with a YM 30 membrane.

6. The concentrated transaminase from the previous step was loaded onto a Sephacryl S-200 column, 2.6×90 cm, in a solution of 0.05M Tris pH 8.0, 0.02 mM pyridoxal phosphate, 1 mM ETDA, and 1 mM beta-mercaptoethanol. Elution with the same buffer gave a band of transaminase activity eluting soon after the void volume. This material was stored at 4° C. and was stable for at least 4 months.

Oxaloacetate decarboxylase can be prepared from Micrococcus luteus, Pseudomonas putida, or the like, by similar procedures as is well known in the art.

EXAMPLE 2

Preparation of L-Phenylalanine

To 0.08 ml of pH 7.0 solution consisting of 50 mM potassium phosphate buffer, 12.5 mM phenylpyruvate, 25 mM L-aspartic acid, 1.25 mM manganese sulfate, 5 mM pyridoxal phosphate, and 1.5 international units of oxaloacetate decarboxylase was added 0.2 ml of a solution at pH 7.0 containing 0.3 international unit (IU) of transaminase. Both immediately, and after incubation at 22° C. for 12 hours, the reaction mixture was assayed for phenylpyruvate. The level of conversion was calculated to be 98.5% based on the amount of phenylpyruvate converted. Amino acid analysis of the reaction mixture showed only two peaks corresponding to L-phenylalanine and unreacted L-aspartic acid. No other amino acid products were detected.

EXAMPLE 3

Immobilization of transaminase and oxaloacetate decarboxylase

An aqueous solution of 2.0 ml of 50 mM potassium phosphate, pH 8.0, containing 1.5 units of transaminase and 5.4 units of oxaloacetate decarboxylase isolated from Micrococcus luteus was added to 5 ml of DEAE-celulose gel (Whatman DE-52) previously equilibrated to pH 8.0 in 50 mM phosphate buffer. After gentle agitation for 5 minutes, assaying for both the transaminase and the oxaloacetate decarboxylase indicated that the enzymes had been adsorbed on the DEAE-celulose and the remaining solution was decanted from the gel.

EXAMPLE 4

Alternative Preparation of L-Phenylalanine

To the immobilized enzyme preparation of Example 3 were added solutions of potassium phosphate, 50 mM, pH 8.0, 2.0 ml; phenylpyruvate, 50 mM, 0.5 ml; and maganese sulfate, 10 mM, 1.0 ml. After a 12 hour incubation, the assay indicated a level of conversion of phenylpyruvate to L-phenylalanine of 96%. This was confirmed by the detection of L-phenylalanine by paper chromatography using an elution solvent of n-butanol:acetone:ammonium hydroxide:water 5:3:1:1. Determination of the amino acid content of the reaction mixture using a Dionex amino acid analyzer showed only two detectable peaks corresponding to L-phenylalanine and L-aspartic acid.

The L-phenylalanine was purified using BioRad AG 50 1×8 20–50 mesh mixed bed ion exchange resin. The crude reaction mixture of pH 8.0 was passed down a column of the resin previously equilibrated to the same pH and the column was eluted first with 2 column volumes of water and then 50 mM potassium phosphate buffer, Ph 8.0. Phenylalanine can be recovered from the eluent by lyophilization or by acidification and crystallization.

EXAMPLE 5

Alternative Preparation of L-Phenylalanine

A 19 ml solution of 50 mM potassium phosphate containing 0.5 mM pyridoxal phosphate, 1 mM $MnSO_4$, 5 international units of transaminase isolated from E. coli, 10 international units of oxaloacetate decarboxylase isolated from Micrococcus luteus, 50 mM phenylpyruvate, and 65 mM L-aspartic acid was incubated at 12 hours at 24° C. At the end of this time, quantitation of the amount of phenylpyruvate by removing a 50 microliter aliquot, diluting to 1.0 ml with 2.5% NaOH, and reading the optical density at 320 nm indicated that all of the phenylpyruvate had been converted to L-phenlalanine. Paper Chromatography on Whatman 3MM paper using butanol:acetone:ammonium hydroxide:water 5:3:1:1 as eluent, followed by staining with 5% ninhydrin dissolved in acetone, showed only two ninhydrin active spots corresponding to unreacted L-aspartic acid and to L-phenylalanine.

EXAMPLE 6

Preparation of L-Tyrosine

A solution buffered at pH 7.0 by 50 mM potassium phosphate containing $MgSO_4$, 1 mM; p-hydroxyphenylpyruvate, 10 mM; L-aspartic acid, 10 mM; transaminase, 0.1 mg/ml; and oxaloacetate decarboxylase isolated from Pseudomonas putida (ATCC 950), 0.1 mg/ml was incubated for 1 hour at 24° C. At the end of this time, assay indicated that no p-hydroxyphenylpyruvate remained. Quantitation of the amount of L-tyrosine produced by the injection of an aliquot in a Dionex amino acid analyzer gave a yield of 99% on a molar basis from p-hydroxyphenylpyruvate.

The L-tyrosine and the pyruvic acid so produced can be purified by a method similar to that used for L-phenylalanine in Example 4 or other methods well known in the art.

EXAMPLE 7

Preparation of L-Tryptophan

A solution of indole-3-pyruvate, 20 mM; L-aspartic acid 20 mM; $MgCl_2$, 1.5 mM; transaminase, 0.3 mg/ml; oxaloacetate decarboxylase, 0.3 mg/ml buffered to pH 7.0 with 5 mM tris-hydroxymethylaminomethane hydrochloride (Tris) was stirred slowly for 2 hours. At the end of this time the reaction is complete. The L-tryptophan and pyruvic acid produced can be purified by methods well known in the art.

EXAMPLE 8

Preparation of L-Leucine

A solution containing $MgCl_2$, 2.5 mM; -2-oxo-4-methylpentanoic acid, 100 mM; L-aspartic acid, 100 mM; transaminase, 1.0 mg/ml; oxaloacetate decarboxylase, 1.0 mg/ml, pH adjusted to 7.0 with NaOH, was stirred slowly at 30° C. for 4 hours. The L-leucine and the pyruvic acid formed can be purified by any methods well known in the art.

EXAMPLE 9

Preparation of L-Valine

A solution containing $MgCl_2$, 2.5 mM; 2-oxo-3-methylbutanoic acid, 100 mM; L-aspartic acid, 100 mM; transaminase, 1.0 mg/ml; oxaloacetate decarboxylase, 1.0 mg/ml, pH adjusted to 7.0 with NaOH, is stirred slowly at 30° C. for 4 hours. The L-valine and the pyruvic acid formed can be purified by any methods well known in the art.

EXAMPLE 10

Preparation of L-Serine

A solution containing $MgCl_2$, 2.5 mM; 3-hydroxypyruvate, 100 mM; L-aspartic acid, 100 mM; transaminase, 1.0 mg/ml; oxaloacetate decarboxylase, 1.0 mg/ml, pH adjusted to 7.0 with NaOH is stirred slowly at 30° C. for 4 hours. The L-serine and the pyruvic acid formed can be purified by any methods well known in the art.

EXAMPLE 11

Preparation of L-Methionine

A solution containing $MgCl_2$, 2.5 mM; -2-oxo-4-thiomethylbutanoic acid, 100 mM; L-aspartic acid, 100 mM; transaminase, 1.0 mg/ml; oxaloacetate decarboxylase, 1.0 mg/ml, pH adjusted to 7.0 with NaOH, is stirred slowly at 30° C. for 4 hours. The L-methionine and the pyruvic acid formed can be purified by any methods well known in the art.

The invention has been described in detail including the preferred embodiments thereof. However, it will be appreciated that those skilled in the art, upon consideration of the disclosure herein, may make modifications and improvements within the spirit and scope of the invention.

What is claimed is:

1. A process for producing alpha amino acids or derivatives thereof, said process comprising reacting an alpha-keto acid with L-aspartic acid in the presence of transaminase enzyme to produce (1) an alpha amino acid corresponding to said alpha-keto acid and (2) oxaloacetate; and decarboxylating said oxaloacetate.

2. The process of claim 1 wherein the said transaminase is a purified or partially purified enzyme preparation, or is contained within a whole cell.

3. The process of claim 1 wherein the said step of decarboxylating oxaloacetate is accomplished using an oxaloacetate decarboxylase enzyme.

4. The process of claim 3 where the said oxaloacetate decarboxylase enzyme is a purified or partially purified enzyme preparation, or is contained within a whole cell.

5. The process of claim 3 wherein said transaminase and said oxaloacetate decarboxylase are each immobilized on an insoluble support.

6. The process of claim 5 wherein said immobilization support is controlled pore ceramic particle or controlled pore glass particle.

7. The process of claim 5 wherein said transaminase and said oxaloacetate decarboxylase are both immobilized on the same support.

8. The process of claim 5 wherein the said transaminase and oxaloacetate decarboxylase are adsorbed on diethylaminoethyl cellulose.

9. The process of claim 1 wherein said transaminase is an aromatic amino acid transaminase.

10. The process of claim 1 wherein said alpha-keto acid is selected from the group consisting of phenylpyruvic acid, p-hydroxyphenylpyruvic acid, 3-(3-indolyl)-pyruvic acid, 3-(4-imidazoyl)pyruvic acid.

11. A process in accord with claim 5 wherein phenylpyruvic acid is reacted with L-aspartic acid in the presence of an aromatic amino acid transaminase and an oxaloacetate decarboxylase, thus producing L-phenylalanine.

12. The process of claim 1 wherein the said transaminase is an enzyme selective for the transamination of amino acids with branched side-chains.

13. The process of claim 1 wherein the said alpha-keto acid is selected from the group consisting of 2-oxo-3-methylbutanoic acid, 2-oxo-4-methylpentanoic acid, 2-oxo-3-methylpentanoic acid, and 3-hydroxypyruvic acid.

14. The process of claim 1 wherein the said transaminase is an enzyme capable of catalyzing the transamination of hydroxypyruvate to L-serine.

15. The process of claim 1 wherein the said transaminase is an enzyme isolated from a microorganism selected from the group consisting of *Escherichia, coli, Bacillus subtilis, Achromobacter eurydice,* or *Klebsiella aerogenes.*

16. The process of claim 3 wherein the said oxaloacetate decarboxylase is an enzyme isolated from a microorganism selected from the group consisting of *Micrococcus luteus, Pseudomonas putida,* or *Azotobacter vinelandii.*

17. The process of claim 3 wherein the said oxaloacetate decarboxylase is reacted in the presence of a metal ion selected from the group consisting of $Mn^{++}$, $Cd^{++}$, $Co^{++}$, $Mg^{++}$, $Ni^{++}$, $Zn^{++}$, $Fe^{++}$, and $Ca^{++}$.

* * * * *